United States Patent [19]

Russo

[11] Patent Number: 4,687,827
[45] Date of Patent: Aug. 18, 1987

[54] BRUSHING CYANOACRYLATES: PACKAGING AND METHOD

[76] Inventor: Libby J. Russo, 3122 Bandera Dr., Palo Alto, Calif. 94304

[21] Appl. No.: 879,820

[22] Filed: Jun. 26, 1986

[51] Int. Cl.⁴ .............................................. B05D 1/28
[52] U.S. Cl. ..................................... 427/340; 427/341; 427/421; 427/429; 424/61; 132/73; 53/431
[58] Field of Search ............... 427/340, 341, 429, 421; 424/61; 132/73, DIG. 3

[56] References Cited

U.S. PATENT DOCUMENTS

| | | | |
|---|---|---|---|
| 4,249,551 | 2/1981 | Nordstrom | 132/73 |
| 4,299,243 | 11/1981 | Umstattd | 132/73 |
| 4,407,310 | 10/1983 | Jadow | 424/61 |
| 4,626,428 | 12/1986 | Weisberg | 424/61 |

Primary Examiner—Shrive P. Beck

[57] ABSTRACT

Normally, cyanoacrylates cannot be applied by brushing since they cure rapidly in contact with brush bristles. By pre-wetting the bristles with a solvent, this curing action is impeded. Thus, brushes so treated can be stored in a cyanoacrylate monomer formulation and the formulation can be brushed.

This discovery permits cyanoacrylates to be conveniently packaged in a bottle with cap and brush ready for use, for example, as fingernail strengthening and extension systems. Thus, sophisticated fingernail enhancement systems can be distributed and used about as conveniently as fingernail polish systems.

7 Claims, No Drawings

BRUSHING CYANOACRYLATES: PACKAGING AND METHOD

BACKGROUND OF THE INVENTION

The present invention relates to a method of applying cyanoacrylates, and, more particularly, to such a method permitting cyanoacrylates to be applied by brushing. While the method has specific application to fingernail extension systems, it also provides for other applications such as the use of cyanoacrylates as coatings and adhesives.

The present invention is targeted primarily at retail packages for fingernail enhancement systems, specifically, fingernail strengthening systems and fingernail extension systems. An object of the present invention is to provide a synergistic combination of product, package and method of application for such systems, as is available for the most widely recognized fingernail enhancement systems, i.e. nail polishes. Fingernail polish is safe and effective for its intended purpose, it is readily applied by brushing, and is conveniently packaged in a small bottle with a brush incorporated with the bottle cap. What is needed is a comparably attractive combination of product, method and packaging for fingernail strengthening and extension systems.

Acrylics have provided a variety of materials pertinent to fingernail strengthening and extension. Some acrylic formulations can be conveniently applied to an existing nail by brushing. Brushable acrylics include anaerobic, reactive and aerobic acrylics, all of which polymerize by a free-radical mechanism.

Polymerization of anaerobic acrylics is normally prevented by the presence of oxygen. Anaerobic acrylics can be formed, for example, by blending a diacrylate or dimethacrylate based on diethylene glycol or higher homologs with a long half-lived hydroperoxide. The very small instantaneous concentration of radicals produced by the homogenous decomposition of the hydroperoxide combines with the diacrylate or alternative to initiate polymerization. However, propagation does not proceed normally in the presence of even small amounts of oxygen which reacts preferentially with the monomer radical to form inactive species.

Anaerobic characteristics can be imparted to several acrylate ester monomers by adding a peroxy polymerization initiator. Examples of suitable monoacrylate ester monomers are furfuryl methacrylate, cyclohexyl acrylate, isobutyl methacrylate, and hydroxyethyl methacrylate.

Even in the absence of oxygen, most anaerobics cure slowly in the absence of accelerators. With the exception of certain "active" metal surfaces, when ions from the surface act as accelerators for the rate of cure, accelerators are generally required for practical cure periods. Anaerobics also generally require surfaces that are clean, free from dirt or grease, and usually mechanically abraded.

From the point of view of fingernail extension procedures, anaerobic acrylics have proved workable but not entirely satisfactory. In the case of a procedure to be applied in a consumer's home, it is generally not practical to provide an oxygen-free cure environment. In addition, the necessity of surface preparation is undesirable.

In contrast to anaerobic acrylics, reactive acrylics depend on the presence of a chemical initiator, not the absence of oxygen, for their cure. Reactive acrylics generally comprise an elastomer colloidally dispersed in a monomer or in a monomer/oligomer/polymer solution. The resultant polymer is toughened by "elastomeric domains" resulting from the dispersed elastomer.

Reactive acrylics generally exhibit a high solvent action allowing the bonding of many unprepared surfaces, even oil contaminated surfaces. Thus, less surface preparation is required for bonding. In part, this is due to the presence of monomers in the reactive acrylic formulations that may dissolve contaminants and may also attack a polymer substrate.

The main disadvantage of reactive acrylics is that the user is required to combine two chemicals, the activator and the acrylic solution. This complicates both the packaging of a fingernail extension system and the application by the user. Furthermore, the strength of the resulting formation is highly dependent on the concentration of activator. This puts a burden on the end user to measure and mix precisely, and this burden may be unacceptable.

Additionally, reactive acrylics tend to be toxic. In some instances this is associated with methylmethacrylate and methacrylic acid monomers. These constituents of many reactive acrylics are toxic with respect to inhalation, ingestion and skin contact and have been rejected for reasons of toxicity on certain production lines. Typically low flash points and the resultant flammability hazard also are significant disadvantages for reactive acrylics. Furthermore, some of the more effective activators, such as dimethyl aniline, are suspected carcinogens.

Aerobic acrylics are similar to reactive acrylics in that they do not require the absence of oxygen or air to cure. Generally they require the use of pre-applied activators to initiate the cure mechanism. These materials are composed of catalysts, elastomeric domain fillers, and low vapor pressure monomers. While these tend to be less toxic than reactive acrylics, the need to combine chemicals remains objectionable.

Some aerobic acrylics are cured by exposure to long wave ultraviolet (UV) radiation. These materials are discussed by Andrew G. Bachman in "Ultraviolet Light Curing 'Aerobic' Acrylic Adhesives", Adhesive Age, December 1982, pp. 31-35. The UV cure avoids the necessity of adding an activator. Furthermore, aerobics tend to be less toxic than the reactive acrylics. Thus, the aerobic acrylics have found a place in fingernail extension systems. However, UV lamps constitute a significant expense. Even when used correctly, UV lamps can be injurious. Furthermore, UV lamps are easily misused and can contribute to burns, eye damage and cancer. Also, the typical 3-5% shrinkage during UV cure can cause unsightly distortions.

Non-acrylic materials, such as formaldehyde resins and free formaldehyde have been used as fingernail strengtheners. However, these materials are carcinogens and impose unacceptable health risks on users.

High quality fingernail extensions and finger nail strengtheners can be formed from cyanoacrylates. Cyanoacrylate formulations have several characteristics which can be exploited by fingernail enhancement systems. Cyanoacrylates cure through a single component process, obviating the need for metering or mixing. Yet, accelerators are generally available where more rapid cure is desired. Even without accelerators, setting can occur in a matter of seconds or minutes, although complete cure can require a day or two. Cyanoacrylate formulations can be 100% reactive, minimizing the need for solvent evaporations and the concomitant health and environmental hazards imposed by such solvents.

Cyanoacrylates have a base of an alkyl 2-cyanoacrylate compound. The versatility of esters of alpha-cyanoacrylic acid, otherwise known as "cyanoacrylates", is well known. These alpha-cyanoacrylate esters may be represented by the general formula:

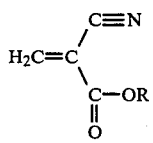

wherein R can be any of various ester substitutions, including —CH$_3$, —CH$_2$CH$_3$, —CH$_2$CH=CH$_2$, and —CH$_2$CH$_2$CH$_3$. When applied in a monomeric form to a surface, they set up rapidly to give a high strength polymer structure, depending on application. The predominant esters are methyl and ethyl, but n-butyl and allyl are used occasionally.

For many years, it has been recognized that the cyanoacrylate esters are polymerized by the presence of —OH groups to form a strong bond in a short period of time without the necessity of a catalyst. Cyanoacrylates polymerize by an ionic mechanism initiated by moisture and basic ions as provided by ammonia or an amine or other organic base. Although the mechanism by which these cyanoacrylates cure is not completely understood, cyanoacrylates appear to polymerize rapidly when spread in a thin film because of facile attack by moisture adsorbed on the substrate surface.

Despite the advantages of cyanoacrylates, their usefulness has been limited by the difficulty in applying the formulations uniformly over a surface. Many people are familiar with the application of cyanoacrylates as glues, such as "Eastman 910" and "Crazy Glue." Such glues are distributed in tubes which can be opened and squeezed to eject the glue like toothpaste is usually squeezed onto a toothbrush. The simile conveys that this method does not yield uniform distribution. It is difficult to squeeze cyanoacrylates accurately and uniformly so as to avoid skin contact and to yield a smooth and level final formation. Thus, it is difficult to achieve an appropriate cosmetic look using this technique.

In the case of their use as glues, cyanoacrylates are often packaged with a plastic "spatula" or spreader, usually built into the cap for the tube. The ejected glue can then be pressed and shoved with this spreader to provide a more even distribution. However, those using this tool and technique have not generally achieved the uniformity desired for fingernail extensions. Other application approaches use squeeze bottles and droppers. These approach generally result in undesirable ridges rather than smooth uniform coats.

Spraying is not a viable approach to applying cyanoacrylates since their rapid cures easily clog spray heads. Also, there is a problem due to the irritation cyanoacrylates can cause to mucous membranes and eyes. While considered safe in contact with fingernails, contact with skin is to be avoided, and propelling the material through the air where it can reach eyes and mouths is dangerous.

A desirable alternative would be to brush cyanoacrylate formulations onto a selected surface. Unfortunately, the cure mechanisms for cyanoacrylates are rapidly activated on a brush, which is rendered useless in a short time. Generally, when one attempts to brush cyanoacrylates, the formulation coagulates and hardens before the formulation can be applied to a surface. While various means can be used to delay curing so that one or two brush strokes may be achieved, the cost involves destruction of a brush with each application.

Thus, what is needed is a synergistic system of product, method and packaging for fingernail extension and strengthening. The product should be relatively safe and effective for strengthening and extending fingernails. The method should be readily implemented and permit the uniform application of the product to a selected surface. The packaging should provide a shelf life appropriate to a consumer product and a convenient form for storing and applying the product.

SUMMARY OF THE INVENTION

In accordance with the present invention, the bristles of a brush are pre-wetted with an anhydrous solvent, e.g. acetonitrile, prior to being saturated with a cyanoacrylate monomer formulation so as to inhibit or retard curing sufficiently to permit the cyanoacrylate to be brushed onto a surface of interest. Likewise, the pre-wetting permits a brush to be stored in a cyanoacrylate monomer formulation for extended durations.

The selected surface can be a fingernail. The method then permits the formation of a smooth fingernail extension or reinforcing coating upon a natural nail. The method can be applied successively to build a more substantial extension.

The pre-wetting can be advantageously used in packaging cyanoacrylates, for example, to be used by consumers in retail fingernail strengthening and extension systems. A bottle or other suitable container holding a cyanoacrylate monomer can have a suitably pre-wetted brush immersed in the cyanoacrylate so as to maintain an extended shelf life. Following the example of packaging for nail polish, it is now practical to supply a consumer with a package with a brush extending from the cap for the bottle or container. The cap should be of a material to which the cyanoacrylate does not readily bond.

In accordance with the present invention, cyanoacrylates can be applied with greater uniformity and control than is possible using squeeze tubes and bottles, droppers, and spatulas that have been used previously. Furthermore, these cyanoacrylates can be packaged in a more convenient and familiar form than has heretofore been practical.

DESCRIPTION OF THE PREFERRED EMBODIMENTS

In accordance with the present invention, the bristles of a brush are pre-wetted with an anhydrous solvent prior to being wetted with a cyanoacrylate monomer formulation. The pre-wetting material is preferably acetonitrile. The pre-wetted brush is preferably damp dried so that it is no longer dripping.

The brush so prepared is then saturated with cyanoacrylate formulation. The brush itself can be any of a wide variety of types. The method of the present invention has been tested successfully with hair, nylon and acrylic fiber brush bristles. Alternatives to acetonitrile solvent include 1,1,1-tricloroethane and dichlorodifluoromethane (Freon) or other fluorinated hydrocarbon. Tests indicate that when this method is used, the cyanoacrylate formulation remains brushable for greater than one half hour.

After application, the cyanoacrylate can be cured by well-known methods. Preferably, the curing is facilitated by misting an accelerator onto the brushed cyanoacrylate. The accelerator can be ammonia, or an amine or other organic base.

This novel method of applying cyanoacrylates permits the formation of nail extensions. It can be used to apply a thin cyanoacrylate layer to strengthen weak fingernails. In addition, the method can be used to cover nail tips and fill ridges. The method then permits the formation of a smooth artificial nail upon a natural nail or other base. The method can be applied successively to build a more substantial fingernail.

The cyanoacrylate can be filled with microspheres of glass or other suitable material to allow for one component application of sculpturing nails. Thus, a convenient and rapid system of fingernail extension or strengthening with relatively low toxicity is provided. In addition, the method of the present invention can be used to brush cyanoacrylates in other contexts. For example, the cyanoacrylates can be used as a coating. Furthermore, the method can be used in bonding two surfaces.

By way of explanation, and not by way of limitation, the cause of the rapid curing of cyanoacrylates on brushes, when the present invention is not applied, is thought to be the thin film effect coupled with exposure to the air and moisture trapped within the brush bristles. On brush bristles, cyanoacrylates form thin films which readily interact with proximate moisture. Presumably, the pre-wetting step inhibits the thin-film effect and displaces these curing agents over the substantial surface area defined by the brush bristles. When the brush is saturated with the cyanoacrylate formulation, the formulation is stable even though the solvent may be absorbed. Thus, curing is significantly retarded adjacent the brush bristles.

The formulations to which the method of the present invention is applied can include compositions comprising at least one monomeric alpha-cyanoacrylate ester of the formula:

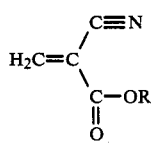

In a preferred embodiment of the present invention, the cyanoacrylate monomer formulation consists of 91% by weight ethyl cyanoacrylate, 5% dimethyl sebacate, 4% poly(methyl methacrylate), 0.1% p-methoxyphenol, and 0.005% sulphur dioxide. Greater viscosity can be achieved using more poly(methyl methacrylate). Some cyanoacrylates suitable for fingernail extension and other applications mentioned herein include: ethyl 2-cyanoacrylate, methyl 2-cyanoacrylate, isobutyl 2-cyanoacrylate, 3-methoxybutyl 2-cyanoacrylate, 2,2,2-trifluoroethyloxyethyl 2-cyanoacrylate, allyl 2-cyanoacrylate, hexyl 2-cyanoacrylate, butyl 2-cyanoacrylate, pentyl 2-cyanoacrylate, decyl 2-cyanoacrylate, octyl 2-cyanoacrylate, chloroethyl 2-cyanoacrylate, butenyl 2-cyanoacrylate, benzyl 2-cyanoacrylate, acetoethyl 2-cyanoacrylate, and phenylethyl 2-cyanoacrylate.

The method of brushing cyanoacrylate described above can be applied by an end-user from a suitably packaged system including the cyanoacrylate formulation, acetonitrile and a brush. The method of brushing cyanoacrylates described above can be applied by an end user from a suitably packaged system including the cyanoacrylate formulation with a brush immersed in the formulation and ready for use. The brush can be an extension of the package cap, similar to the arrangement common for fingernail polish bottles and packages.

The cap and/or the bottle containing the brush and cyanoacrylate can advantageously be of material to which cyanoacrylate does not bond so that the cap does not become bonded to the bottle. For example, the cap can be of polypropylene. Alternative materials to which cyanoacrylates do not readily bond include polyethylene, EPDM rubber, and plasticized PVC.

Thus, the present invention provides a novel packaging scheme for cyanoacrylates. A package with a bottle containing cyanoacrylate monomer, a cap and a pre-wetted brush immersed in the cyanoacrylate, heretofore unknown and impractical, has now been achieved. Tests have indicated that this is a shelf-stable system. Thus, it is now possible to package cyanoacrylate in a convenient and familiar form, i.e., in a package analogous to that commonly used for fingernail polish. As indicated above, the cap, and the container as well, can be of polypropylene or other material to which cyanoacrylates do not readily bond.

The shelf life of cyanoacrylates can be enhanced by the addition of polymerization inhibitors or stabilizers. Suitable examples include anionic polymerization inhibitors such as sulphur dioxide, nitrogen oxide, boron trifluoride, and free radical stabilizers such as hydroquinone, monomethylether or hydroquinone, nitrohydroquinone, and hydroquinone monoethylether.

It is also possible to treat a cyanoacrylate formulation to minimize its water content. Most cyanoacrylate preparations contain several hundred parts per million (ppm) of water. Since moisture initiates polymerization and then deteriorates the polymerized resultant, it is preferable to eliminate water from the cyanoacrylate in so far as possible.

Methods of producing cyanoacrylates often involve the condensation of an ester of cyanoacetic acid with formaldehyde followed by pyrolysis of the intermediate to yield the cyanoacrylate. Reduced water content can be achieved by performing all steps including and after pyrolysis under dry conditions. All equipment and reagents used during pyrolysis and the following steps must be carefully dried and all transfer steps need be performed in a dry, inert gas atmosphere.

The drying operation advantageously consists of heating the equipment, preferably under vacuum, followed by a thorough flushing with a dry inert gas. Other drying procedures can be used. The cyanoacrylate should be maintained in a dry inert gas atmosphere at all time. All materials which are used during the pyrolysis step and later, such as inhibitors, are dried. Standard drying procedures are adequate. The cyanoacrylate formulation is then transferred and packaged in dry containers under a dry, inert gas atmosphere. The resulting cyanoacrylate contains less than about 200 ppm water and has good activity for up to 2 years and longer. This method is further detailed in U.S. Pat. No. 3,728,375 to Coover, Jr. et al.

Additives such as thickening agents, plasticizers, and the like can be added according to the intended application for the cyanoacrylate. Examples of suitable plasticizers include esters of cyanoacetic acid, succinic acid, sebacic acid and phthalic acid, glycerine triacetate, and glycerine tributyrate. Where greater viscosity is desired, thickening agents or viscosity increasing agents can be added to the stabilized cyanoacrylate formulation. A preferred thickener is poly(methyl methacrylate). Other thickening agents are poly-α-cyanoacrylates, polyacrylates, polymethacrylates, cellulose acetates, and similar cellulose esters as well as other polymer materials which do not react with the monomers causing a premature cure and which preferably can be mixed with said monomers.

Body can be added to the cyanoacrylates, for example, by incorporating glass microspheres. Various dyes can be added to impart color.

More generally, other applications are provided for by the present invention. Artists desiring rapid curing paints now have better control. An artist can brush paint with cyanoacrylates and spray with an accelerator so as to effect an essentially immediate cure. The cyanoacrylate formulation can be filled with a conductor such as gold or silver to paint conductive lines on printed circuit boards and elsewhere. Since the cyanoacrylates are effective adhesives, such a conductive formulation can also be used as a low temperature solder. The cyanoacrylate can also be used as a protective coating in many applications, such as the strengthening of weak fingernails. Accordingly, the scope of the present invention is limited only by the following claims.

What is claimed is:

1. A method of applying cyanoacrylate to a selected surface, said method comprising the steps of:
   pre-wetting the bristles of a brush with a solvent for cyanoacrylate;
   immersing the bristles of the pre-wetted brush with a cyanoacrylate monomer formulation; and
   brushing the cyanoacrylate formulation onto a selected surface.

2. The method of claim 1 further characterized in that the solvent is acetonitrile.

3. The method of claim 1 further comprising the step of damp drying the solvent after the pre-wetting step and before the immersion step.

4. The method of claim 1 iterated, with each application of cyanoacrylate defining the selected surface for the next application.

5. The method of claim 1 further comprising the step of curing the brushed cyanoacrylate.

6. The method of claim 1 further comprising the step of applying an accelerator to the cyanoacrylate formulation after brushing.

7. The method of claim 6 further characterized in that the accelerator is sprayed onto the cyanoacrylate formulation.

* * * * *